(12) United States Patent
Williams

(10) Patent No.: US 12,714,646 B2
(45) Date of Patent: Aug. 25, 2026

(54) INTERLOCKING VIAL SLEEVE APPARATUS FOR MEDICATION MANAGEMENT

(71) Applicant: Adam Williams, Brooklyn, NY (US)

(72) Inventor: Adam Williams, Brooklyn, NY (US)

( * ) Notice: Subject to any disclaimer, the term of this patent is extended or adjusted under 35 U.S.C. 154(b) by 341 days.

(21) Appl. No.: 18/472,507

(22) Filed: Sep. 22, 2023

(65) Prior Publication Data

US 2025/0099330 A1 Mar. 27, 2025

(51) Int. Cl.
*A61J 1/16* (2023.01)
*C12N 5/00* (2006.01)

(52) U.S. Cl.
CPC ................ *A61J 1/16* (2013.01); *C12N 5/548* (2025.01)

(58) Field of Classification Search
CPC .. A61J 1/16; C12N 5/54; C12N 5/548; B65D 11/00–1893
USPC .................................................. 220/737, 740
See application file for complete search history.

(56) References Cited

U.S. PATENT DOCUMENTS 10,898,411 B1 * 1/2021 Born ...................... B65D 23/12
2008/0164273 A1 * 7/2008 Dallman ............... A61J 7/0069 221/2
2013/0213846 A1 * 8/2013 Hendrickson ............. E04B 2/08 206/509
2014/0326693 A1 * 11/2014 Martin .............. B65D 21/0231 215/10
2015/0209790 A1 * 7/2015 Sharpe ...................... A61J 1/16 422/562
2017/0095403 A1 * 4/2017 Larson .............. B65D 23/0885
2022/0408917 A1 * 12/2022 Paulick .................. A47F 7/283

* cited by examiner

*Primary Examiner* — Susan S Su
(74) *Attorney, Agent, or Firm* — Mohamed C. Azeez

(57) ABSTRACT

A protective sleeve apparatus for multiple vial carriage, said apparatus comprising: a pliable enclosure (sleeve), wherein said sleeve is comprised of a first surface, second surface, and at least three side walls adjoining the first surface with the second surface to form the sleeve; at least one aperture disposed on at least one of the first and/or second surface of the sleeve, wherein said aperture is configured for an insertion or removal of the glass vial into the sleeve; and at least one means of interlocking the sleeve with at least a second sleeve, wherein the interlocking component is disposed on at least one of the side walls of either of the two sleeves, whereby the interlocked sleeves enable protective multiple vial carriage.

10 Claims, 8 Drawing Sheets selecting a thermoplastic material engineered to impart at least one of shock-absorption, flexibility, thermal stability, and UV-resistance to the sleeve; 72

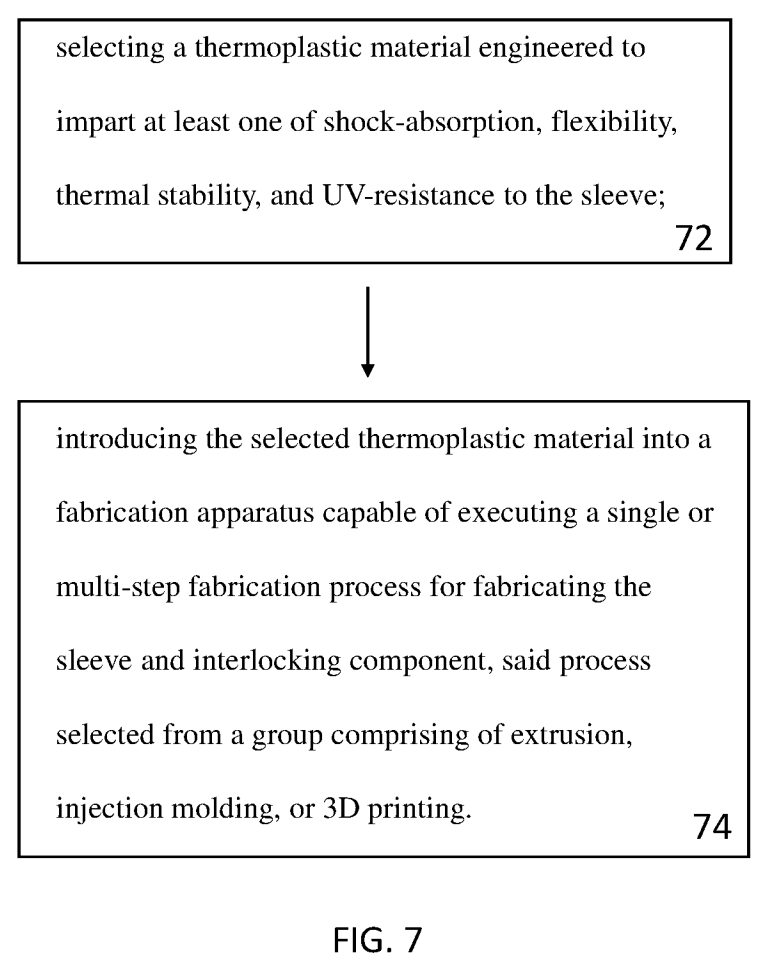

↓ introducing the selected thermoplastic material into a fabrication apparatus capable of executing a single or multi-step fabrication process for fabricating the sleeve and interlocking component, said process selected from a group comprising of extrusion, injection molding, or 3D printing. 74

FIG. 7

INTERLOCKING VIAL SLEEVE APPARATUS FOR MEDICATION MANAGEMENT

FIELD OF INVENTION

The invention pertains generally to the field of medical apparatus, and more particularly, to a protective vial sleeve configured for interlocking.

BACKGROUND OF INVENTION

The use of glass vials for storing and transporting sensitive medical solutions such as insulin, vaccines, and other injectable medications is both widespread and indispensable. The inert nature of glass ensures that the stored substance remains uncontaminated and preserves its medicinal integrity over time. However, the fragility of glass poses a significant problem, especially in environments where drops or accidental impacts are likely. A broken vial can result not only in the loss of expensive or life-saving medication but also poses a safety risk due to shattered glass.

To mitigate these concerns, protective sleeves have been developed. Typically made of resilient materials like silicone or thermoplastic polyurethane (TPU), these sleeves are designed to cushion glass vials from falls or impacts, significantly reducing the risk of breakage. Although protective sleeves have proven effective in reducing the physical risks to individual vials, they introduce another set of challenges when it comes to the organization and carriage of multiple vials.

Presently, for those who require multiple vials, whether for different medications or multiple doses of a single medication, organizing and transporting these vials is often cumbersome. Existing solutions usually involve the use of a larger carrying case or block with built-in compartments to house each vial separately. While these blocks do provide a level of protection and organization, they come with their own sets of drawbacks. For one, these storage blocks can be bulky and inconvenient to carry, particularly for patients who are already burdened with other medical supplies or personal items. Additionally, since all vials are stored in a single block, there is an increased risk of vial confusion. Patients or healthcare providers might accidentally pick the wrong vial, especially if multiple medications look similar or if the block's design makes it difficult to view labels easily.

Furthermore, these blocks are often rigid and allow little room for flexibility in terms of the number and arrangement of vials. Patients or healthcare providers who need to carry a varying number of vials find it challenging to adapt such rigid systems to their changing needs. Moreover, the compartments in these blocks are often designed for vials of a specific size or shape, making them less versatile for vials of different dimensions.

Another notable limitation is that these blocks seldom offer a convenient way to carry or organize associated accessories, like syringes, which are often necessary for administering the medications stored in the vials. While some specialized cases provide separate compartments for syringes, they add to the overall bulk and complexity of the system.

In summary, while protective sleeves for individual vials have come a long way in minimizing the risk of glass breakage, the current medication management solutions are far from ideal. They are often bulky, lack flexibility, and raise the risk of vial confusion due to their design. What is clearly needed is an innovative solution that not only offers the protective advantages of a sleeve but also addresses the pressing issue of organizing and transporting multiple vials in a convenient, flexible, and user-friendly manner. Unlike existing block-based solutions, an ideal medication management solution should facilitate modular, customizable arrangements for multiple vials, allowing for easy identification and access while minimizing the risk of confusion and error.

There is sorely a need for a novel solution aimed at addressing the unmet needs in the realm of protective vial sleeves, particularly focusing on ease of use, modularity, and the prevention of vial confusion in the management of a patients' medication regiment.

SUMMARY

These and other features and improvements of the present application will become apparent to one of ordinary skill in the art upon review of the following detailed description when taken in conjunction with the several drawings and the appended claims. This invention relates to the interlocking of multiple protective sleeves for glass vials in order to achieve vial chaining as a solution for multiple vial carriage or organization.

In a generalized aspect, a protective sleeve apparatus is described that facilitates the carriage of multiple medical vials in a chained or interconnected arrangement (vial chain, chaining). This sleeve is made from a pliable material like thermoplastic polyurethane or silicon, designed to encase each medical vial. The sleeve features at least one aperture on its surface to allow for the insertion or access of the vial, and optionally, for viewing the vial's label.

In another generalized aspect, a method for manufacturing such protective sleeves is disclosed. The selected thermoplastic material is chosen to impart properties like shock-absorption, flexibility, thermal stability, or UV-resistance. The material is then introduced into a fabrication apparatus that can execute various manufacturing techniques such as extrusion, injection molding, or 3D printing.

In an aspect, the sleeve includes an interlocking component featuring a positive and negative feature coupling mechanism. This allows for secure coupling of multiple sleeves through mechanical means, such as protrusions and recesses, effectively creating a chained arrangement of vials.

In another aspect, the material of the interlocking component is designed to have a higher tensile value than the remainder of the sleeve. This design choice adds extra durability and strength to the interlocking points, improving the overall reliability and longevity of the chained vial arrangement. In a further aspect, the interlocking component and the main body of the sleeve are comprised of the same pliable material but maintain similar tensile values. This results in a uniform distribution of material properties across the entire sleeve, ensuring consistent performance during usage.

In yet another aspect, the positive feature of the coupling mechanism is located on one fixed side of the sleeve, and the negative feature is placed on the opposite fixed side. This arrangement allows for the seamless and secure chaining of multiple vials, making the system easy to assemble and disassemble. In a different aspect, one surface of the sleeve is dedicated specifically to housing a syringe. This provides a comprehensive solution for the storage and transportation of medical supplies, incorporating both vial and syringe storage in a single unit.

In an alternative aspect, the sleeve apparatus is designed to accommodate an indefinite number of vials. This offers a highly customizable and flexible solution for users who need to carry various numbers and types of medications.

In a more detailed aspect, multi-component injection molding is used as a manufacturing method. This allows the fabrication of the interlocking component from a material with a higher tensile value than the remaining sleeve, thereby providing added durability to the assembly.

In another detailed aspect, the interlocking component can also be configured to serve as an ergonomic handle. This feature adds an extra layer of convenience and ease of use for the end-user, simplifying the process of carrying and accessing the vials.

In a further detailed aspect, the interlocking component includes tactile features designed to assist visually impaired users. These tactile indicators help in correctly orienting and engaging the sleeve, enhancing its usability. In an additional detailed aspect, the interlocking component is designed to lock with a compatible carrying case. This provides a secondary means of storage and transport, further enhancing the sleeve's versatility.

In a specialized aspect, the interlocking mechanism can be designed to organize the vials either in a linear or angular array. This arrangement aids in inventory management for healthcare professionals or for individual users who are managing multiple medications. In a distinct specialized aspect, a quick-release feature is incorporated into the interlocking mechanism. This feature becomes invaluable in emergency medical situations, where rapid access to medications could be crucial.

In the most expansive aspect, the sleeve can feature any number of surfaces or points for a range of functionalities, including aperture insertion, vial access, interlocking, and syringe housing. This makes the sleeve a highly flexible and comprehensive solution for various vial storage and transport needs.

In a final generalized aspect, various material options are disclosed for the sleeve, such as elastomers, thermoplastics, synthetic rubbers, specialty polymers, or composites. Additionally, alternative means for interlocking, like magnetic coupling, clips, hook and loop closure, snap-fit connection, or bonded assembly, are considered, broadening the applicability of the sleeve in different scenarios.

Further advantages and novel features of the invention will be set forth in part in the description that follows, and in part will become more apparent to those skilled in the art upon examination of the following or upon learning by practice of the invention.

BRIEF DESCRIPTION OF FIGURES

FIG. 7 depicts an exemplary method flow diagram of the method of manufacturing of a protective vial sleeve in accordance with an aspect of the invention.

DETAILED DESCRIPTION

Figure 1B:
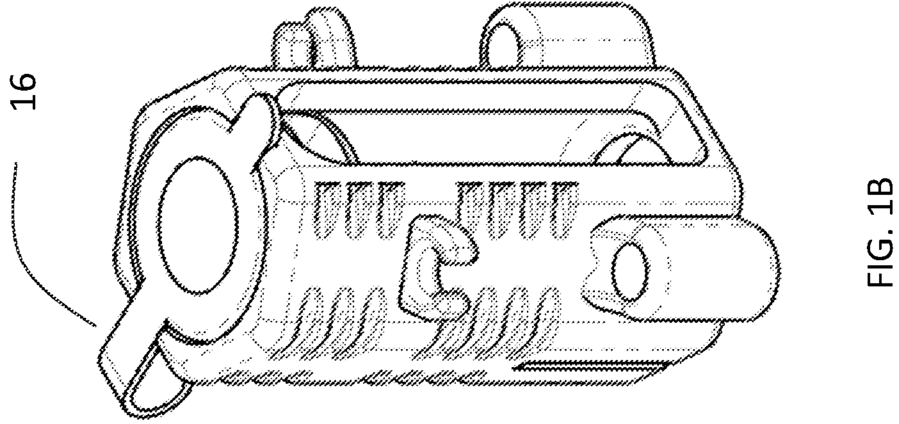
FIG. 1B depicts an exemplary protective vial sleeve in an isometric view in accordance with an aspect of the invention.

Numerous embodiments of the invention will now be described in detail with reference to the accompanying figures. The following description of the embodiments of the invention is not intended to limit the invention to these embodiments but rather to enable a person skilled in the art to make and use this invention. Variations, configurations, implementations, and applications described herein are optional and not exclusive to the variations, configurations, implementations, and applications they describe. The invention described herein can include any and all permutations of these variations, configurations, implementations, and applications.

In the following description, numerous specific details are set forth in order to provide a thorough understanding of the invention. It will be apparent, however, to one skilled in the art that the invention can be practiced without these specific details.

Reference in this specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but no other embodiments.

In an embodiment, the invention is a protective sleeve apparatus for multiple vial carriage or vial chaining, presenting a pivotal advance in medication management. This apparatus is comprised of a pliable sleeve designed to protectively encase a medical vial. It offers more than mere protection; the sleeve is built with specialized surfaces that add layers of utility. Specifically, the sleeve has at least one surface or point with an aperture for at least one of the following: vial insertion into the protective sleeve, vial access for drawing vial contents, or viewing a label and/or quantity of content in the vial.

Furthermore, the sleeve features another surface or point, specifically dedicated to interlocking with a counter surface or point of at least a second protective sleeve. This innovative feature is the key to "vial chaining" in a linear or angular fashion as a medication management solution that provides a more organized and efficient way to store and transport multiple vials.

The shape of the protective sleeve is also highly adaptable. Though any number of polygonal shapes are possible, the preferred embodiment employs a hexagonal design. This geometry provides six surfaces that can be utilized for multiple functions. These can include opposable surfaces dedicated for syringe holder assembly and opposable interlocking surfaces for chaining together multiple vials.

The protective sleeve can be made from various pliable materials such as thermoplastics or silicone. These materials are chosen for their advantageous properties, including flexibility, durability, and ease of sterilization, contributing further to efficient medication management.

In summary, this protective sleeve apparatus revolutionizes medication management by offering a versatile, multi-functional, and secure method for the storage and transportation of medical vials. It directly addresses the challenges of modern healthcare environments, providing features like multi-purpose apertures and the innovative concept of vial chaining.

Figure 1A:
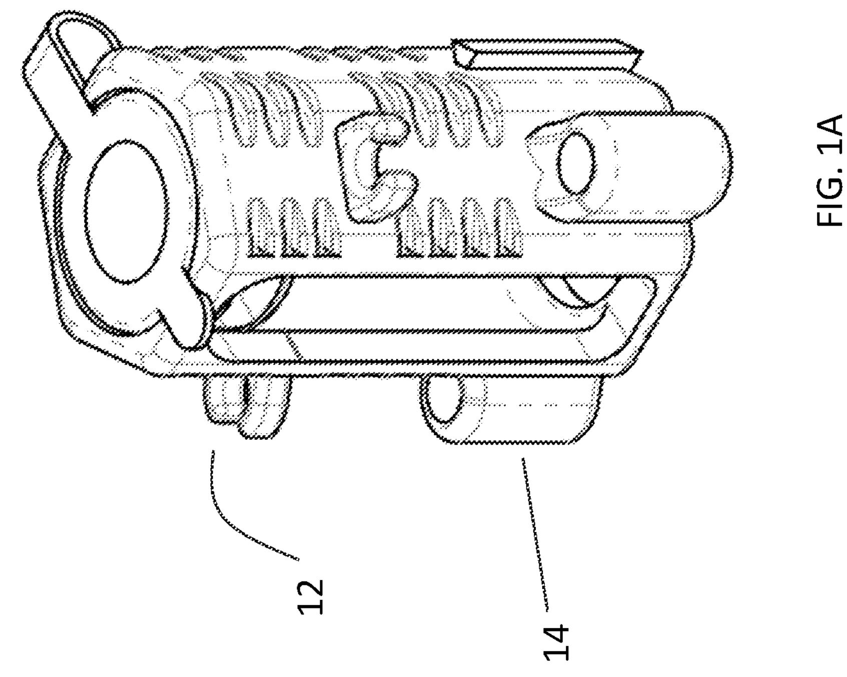
FIG. 1A depicts an exemplary protective vial sleeve in an isometric view in accordance with an aspect of the invention.

In an embodiment, FIG. 1A provides an isometric perspective of a protective sleeve specially designed to securely house a medical vial. The figure prominently features a syringe holder support arm 12, extending vertically from a base 14. The syringe holder support arm 12 is constructed to maintain a syringe in an upright position, in immediate reach and sterile conditions, next to the medical vial it is intended to interact with. In an embodiment, the base 14 serves as a stable foundation for the syringe holder support arm 12. Its primary function is to maintain the syringe in a stable, vertical position, mitigating the risk of toppling or other accidental dislodgements.

In an embodiment, the protective sleeve is fabricated from a thermoplastic material. This material confers several advantages such as durability, impact resistance, and chemical inertness, making it highly suitable for medical applications. In an embodiment, pliable materials like silicone or TPU (Thermoplastic Polyurethane) are also suitable construction materials for the sleeve. These materials are advantageous for their flexibility and soft texture, qualities that facilitate ease of handling and adaptability to different vial shapes.

In an embodiment, FIG. 1B illustrates a top access tethered lid 16. This lid is hinged, allowing for secure sealing and easy access to the medical vial stored within the sleeve. The lid 16 serves the dual purpose of protecting the vial from contamination and providing easy access when the vial is needed.

In an embodiment, the sleeve may adopt a variety of polygonal shapes, including hexagonal configurations. These different shapes allow for various surface options such as a viewing aperture surface, specialized opposable surfaces dedicated to an interlocking feature, and optionally a stand-alone or opposable syringe-holder assembly surface/s.

Figure 2B:
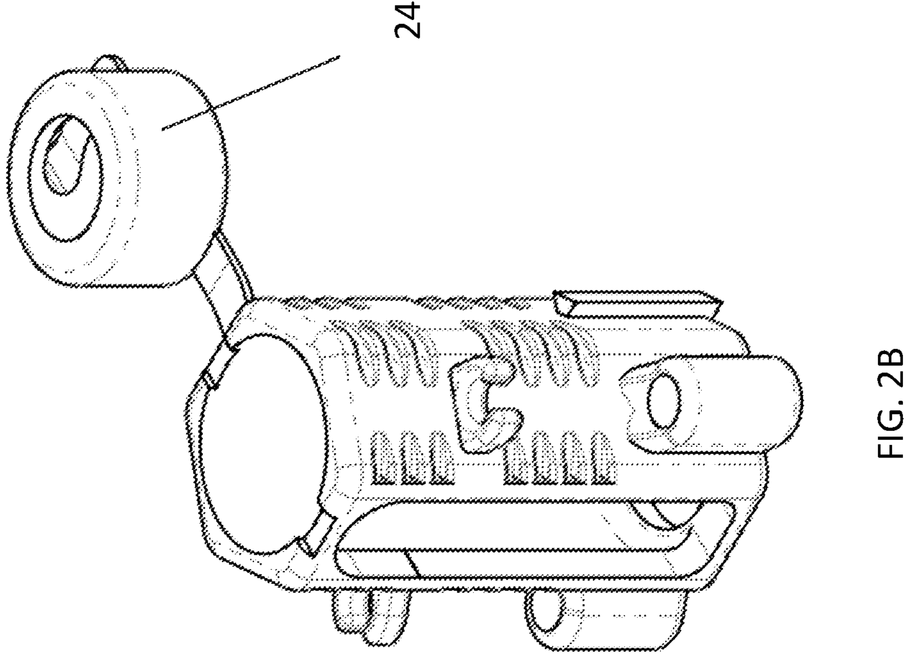
FIG. 2B depicts an exemplary protective vial sleeve in an isometric view in accordance with an aspect of the invention.
Figure 2A:
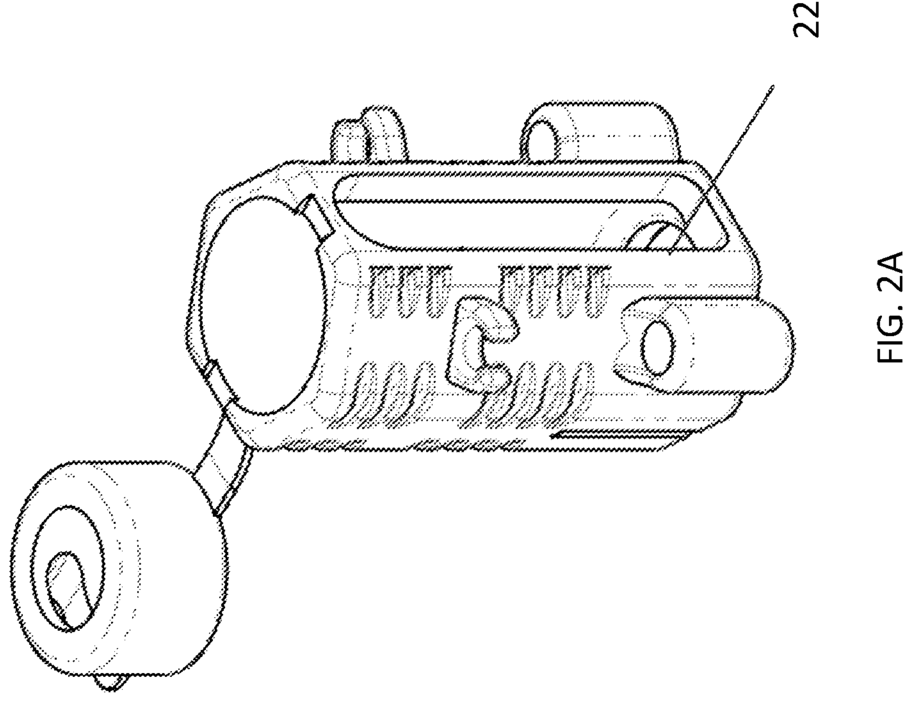
FIG. 2A depicts an exemplary protective vial sleeve in an isometric view in accordance with an aspect of the invention.

Now in reference to FIGS. 2A and 2B, which both are once again an isometric view of the same protective vial sleeve for interlocking sleeves (vial chaining) as a medication management solution. Now in reference to FIG. 2A and FIG. 2B, these figures serve as illuminative extensions to FIG. 1A and FIG. 1B, providing more nuanced insights into the protective sleeve apparatus and its utility in medication management.

In an embodiment, FIG. 2A specifically emphasizes the front aperture for viewing 22, distinct from the aperture used for vial insertion. This dedicated viewing aperture allows for a quick and accurate visual identification of the vial contents or label, streamlining the medication verification process for healthcare providers.

In an embodiment, FIG. 2B showcases the underside of the tethered lid 24, which has been engineered to provide a medical-grade seal for the vial. Notably, this tethered lid 24 is associated with a separate aperture designed for accessing the vial. When closed, the lid offers a reliable, sterile seal that maintains the integrity of the vial's contents.

In an embodiment, both FIG. 2A and FIG. 2B bring attention to the utility of the protective sleeve apparatus in vial chaining. The ability to interlock multiple sleeves can significantly facilitate medication management, for individual patients, and clinicians alike. Vials can be arranged either linearly or angularly, thanks to the polygonal shape of the sleeves. This kind of modular arrangement is especially beneficial for managing multiple medications, as it allows healthcare providers to efficiently organize, identify, and access vials.

In an embodiment, the polygonal shape of the sleeve, as per the preferred hexagonal design, offers structural benefits that go beyond mere aesthetics or easy handling. For instance, the shape can enable more efficient stacking for storage, which is another consideration in medication management. The geometric alignment made possible by the polygonal design creates a stable structure that can be safely stored without rolling or tipping, thus enhancing both storage efficiency and safety.

Figure 3B:
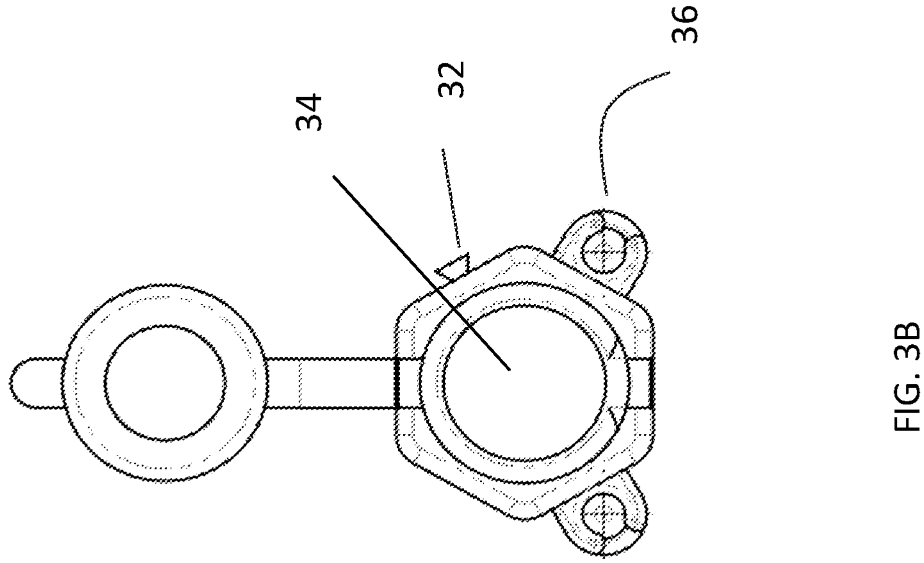
FIG. 3B depicts an exemplary plan view of a protective vial sleeve in accordance with an aspect of the invention.
Figure 3A:
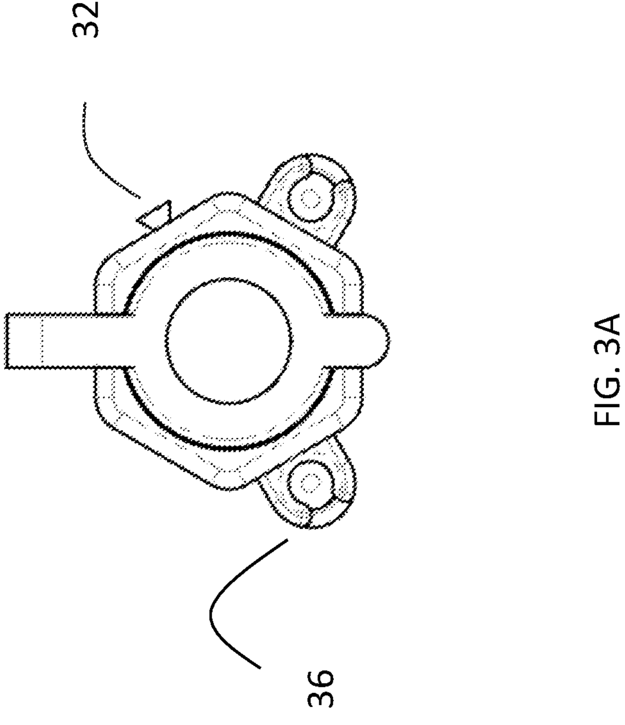
FIG. 3A depicts an exemplary plan view of a protective vial sleeve in accordance with an aspect of the invention.

Now in reference to FIG. 3A and FIG. 3B, these figures offer plan views of the protective sleeve apparatus, further clarifying its structure and potential utility in medical settings. In an embodiment, FIG. 3A focuses on the top access aperture for accessing the vial 34 with the tethered lid in a closed position. This serves to reinforce the sealing capability of the apparatus, ensuring that the medical-grade seal effectively maintains the sterility and integrity of the vial's contents until they are needed, minimizing the risk of contamination.

In an embodiment, FIG. 3B displays the protective sleeve with the tethered lid in an open position. Here, the focus is still on the top access aperture 34, but now it demonstrates the ease with which the vial can be accessed. When open, the tethered lid allows for uncomplicated, yet secure, access to the vial, making the drawing or injecting of its contents straightforward.

In an embodiment, both FIG. 3A and FIG. 3B feature the syringe holder 36, displayed on opposable surfaces of the sleeve. This design allows for ergonomic and efficient organization of the syringes in relation to the vials, further aiding in medication management. The placement and orientation of these syringe holders can be crucial in high-demand medical environments where rapid, accurate medication administration is a priority.

In an embodiment, FIG. 3A also calls attention to a single surface 32 where the positive feature of the interlocking component is visible. Though the opposable negative feature for interlocking is not shown in these plan views, its existence is implied, further contributing to the modularity and adaptability of the protective sleeve design. This unique interlocking feature supports the concept of vial chaining, where multiple sleeves can be connected either linearly or angularly for streamlined medication management.

Figure 4:
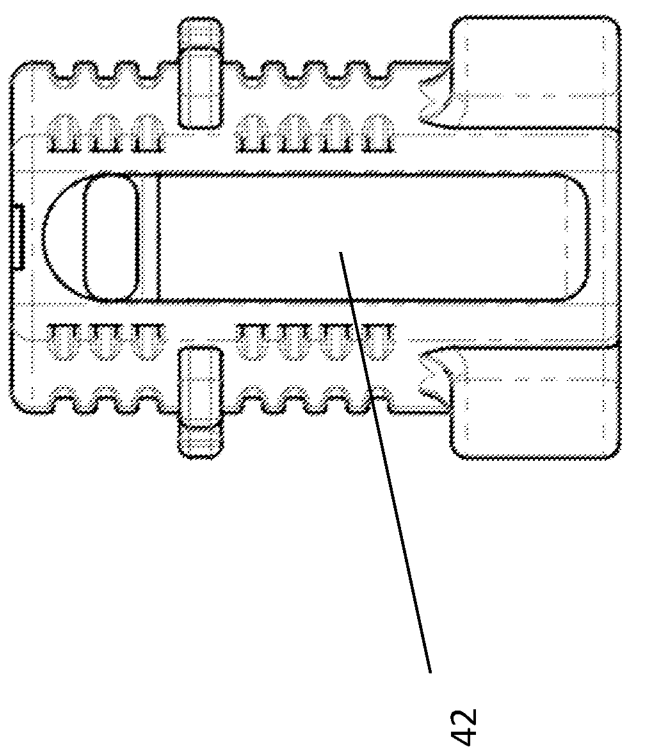
FIG. 4 depicts an exemplary front elevation view of a protective vial sleeve in accordance with an aspect of the invention.

In continuing reference to the versatility of the protective sleeve, FIG. 4 illustrates a front elevation view of the protective sleeve in accordance with an aspect of the invention. The front aperture 42 for label and content levels viewing of the vial may optionally double as the insertion aperture—or even access aperture—for enabling insertion and, or access of the vial by a patient or care provider.

Figure 5:
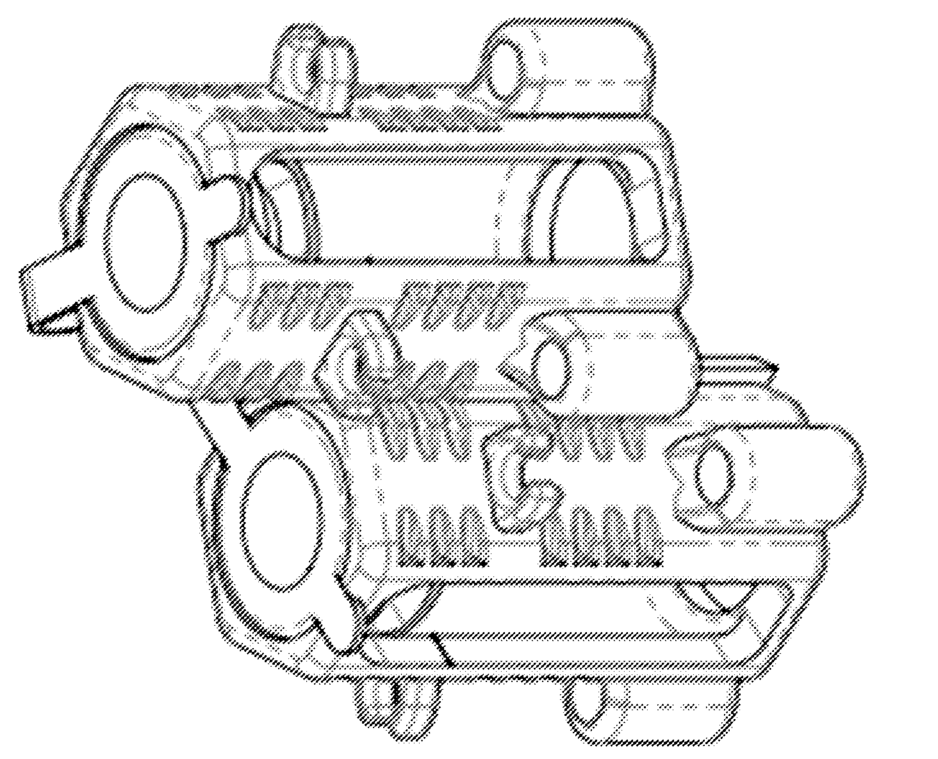
FIG. 5 depicts an exemplary isometric view of interlocked protective vial sleeves (vial-chained) in accordance with an aspect of the invention.
Figure 6:
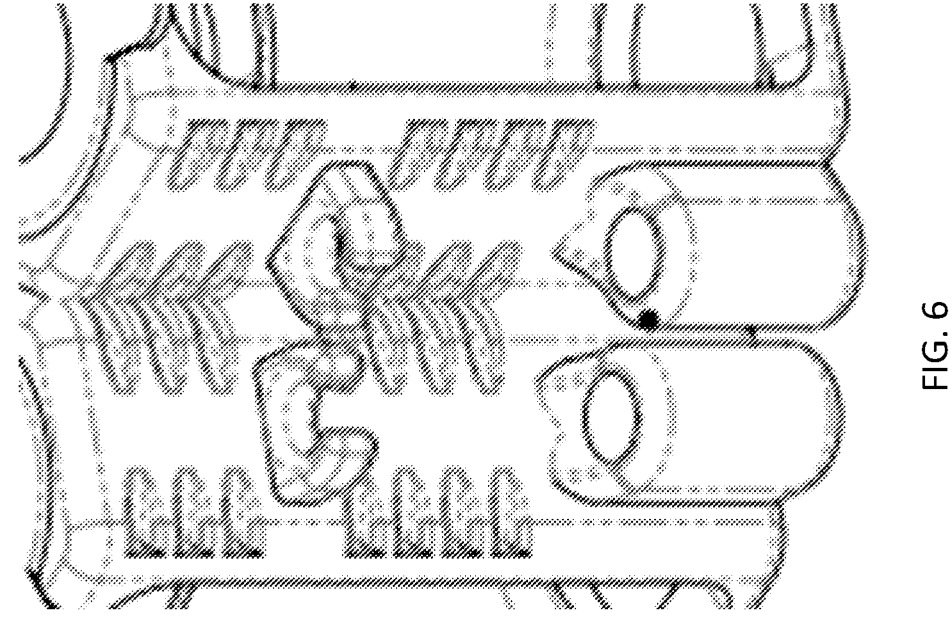
FIG. 6 depicts an exemplary sectional view of the interlocking component of the chained vial sleeves in accordance with an aspect of the invention.

Now in reference to FIG. 5 and FIG. 6, the illustrations emphasize the adaptability and utility of the interlocking component, specifically as it relates to medication management for both healthcare administration and individual users.

In an embodiment, FIG. 5 graphically demonstrates how multiple sleeves can interlock in a chain-like formation. The method of this embodiment further includes configuring the interlocking component to organize vials in either a linear or angular array. This versatility facilitates better inventory management for healthcare professionals and offers users with multiple medications a systematic way to manage their medical regimen.

In an embodiment, FIG. 6 presents a sectional view that gives insight into the mechanics of the interlocking feature. While in some embodiments, the sleeve fabrication may involve using a higher-tensile thermoplastic material for fabricating the interlocking component, employing a multi-step fabrication process that may include multi-component injection molding. This process allows the interlocking component to be fabricated from a material with higher tensile value compared to the remaining sleeve. The result is a more durable and resilient interlocking system that can withstand frequent usage, ideal for healthcare settings where reliability is paramount.

However, as shown in FIGS. 5 and 6, the protective sleeve apparatus and the interlocking component are fashioned from a single-step continuous thermoplastic polymer. This material choice not only simplifies the manufacturing process but also ensures that both the sleeve and the interlocking component share identical or similar tensile values. This uniformity in material properties offers a streamlined approach to design and production, eliminating the complexities associated with multi-component injection molding or different materials. The result is a cohesive and harmonious system where the sleeve and interlocking component function seamlessly together, providing a reliable and robust solution for medication management.

In another embodiment, the interlocking component is configured to also serve as an ergonomic handle, further adding to its functionality and user-friendliness. This configuration makes it easier to handle individual vials, particularly useful for healthcare providers during fast-paced, demanding conditions.

In yet another embodiment, the interlocking feature includes a tactile element designed to assist visually impaired users. This tactile feature ensures proper orientation and engagement with the sleeve, thereby reducing the chances of errors.

Furthermore, the interlocking component can be configured to interact with a compatible carrying case, adding another layer of utility for storage or transportation. This embodiment offers an additional layer of organizational capability, further supporting medication management tasks such as inventory tracking and secure storage.

In a different embodiment, the interlocking mechanism is designed for quick-release detachment, allowing for ease of use in emergency medical scenarios where rapid access to medication is crucial.

The protective sleeve apparatus comprises an enclosure fabricated from materials like elastomers, thermoplastics, synthetic rubbers, specialty polymers, or composites. These materials endow the sleeve with properties like shock absorption, flexibility, thermal stability, and UV resistance. The means for interlocking can vary, including but not limited to positive and negative feature interlocking, magnetic coupling, clips, hook and loop closure, snap-fit connections, or bonded assembly. This flexibility in design adds to the overall utility, covering a wide array of needs in medication management, including storage efficiencies and inventory tracking in healthcare administration, as well as aiding individual users in the safe and effective management of their medications.

FIG. 7 illustrates a high-level or exemplary method flow diagram detailing the steps involved in the fabrication of the interlocking protective sleeve for achieving vial chaining for medication management solutions. As illustrated, the exemplary fabrication method entails the steps of: (1) selecting a thermoplastic material engineered to impart at least one of shock-absorption, flexibility, thermal stability, or UV-resistance to the sleeve; and introducing the selected thermoplastic material into a fabrication apparatus capable of executing a single or multi-step fabrication process for fabricating the protective sleeve with an interlocking component for interlocking multiple protective sleeves for achieving vial chaining, said process selected from a group comprising of extrusion, injection molding, or 3D printing.

FIG. 7 offers a comprehensive, high-level method flow diagram that outlines the multifaceted fabrication process for creating the interlocking protective sleeve. This sleeve is designed to revolutionize the way medical vials are managed, stored, and accessed, thereby serving as a linchpin in medication management solutions. One of the most intriguing aspects of this embodiment is its compatibility with 3D printing technology, a process that affords an extraordinary level of customization and precision.

The method commences with the careful selection of a thermoplastic material, tailored to infuse the sleeve with desired characteristics such as shock absorption, flexibility, thermal stability, and UV resistance. It is crucial to note that when 3D printing is the chosen method of fabrication, this material is commonly available in the form of a filament or resin, optimized for 3D printing applications.

Once the ideal thermoplastic material is chosen and prepared in the appropriate form, it is then fed into a 3D printer. Modern 3D printers are astonishingly versatile, capable of executing complex geometries and fine details, making them perfectly suited for creating intricate components like the interlocking feature in these sleeves. The 3D printer operates under computer control, following a digital model to lay down successive layers of material, building the sleeve and its interlocking component from the ground up.

The advantage of utilizing 3D printing in this context is manifold. First, it allows for rapid prototyping; tweaks in the design can be made on the fly, with real-world tests of the sleeve conducted in between print runs. Second, 3D printing enables the production of highly customized sleeves, potentially tailored to fit specific vial types or to integrate unique interlocking mechanisms. Third, 3D printing is exceptionally scalable, whether you're producing a single sleeve for proof-of-concept or ramping up for a larger production run.

3-D printing technology may be a viable and an affordable alternative to injection production methods. The steps involved in 3D printing technology may be comprised of: (1) producing a 3-D model using computer-aided design (CAD) software, (2) convert the CAD drawing to the STL (standard tessellation language) format, (3) transfer to AM machine and STL file manipulation thereby designating the size and orientation for printing, (4) preparing the machine for a new print job including, but not limited to, refilling polymers, binders, tray to serve as a foundation and other consumables for the printer use, (5) building the prototype, (6) removing the printed object from the printer and (7) post-processing the printed object including, but not limited to, brushing off any remaining powder or bathing the printed object to remove water-soluble supports.

In summary, the 3D printing process, as illustrated in this particular embodiment detailed in FIG. 7, offers an unparalleled combination of customization, precision, and scalability. It not only makes the fabrication of these revolutionary interlocking protective sleeves feasible but optimizes them to contribute effectively to medication management solutions.

Figure 8:
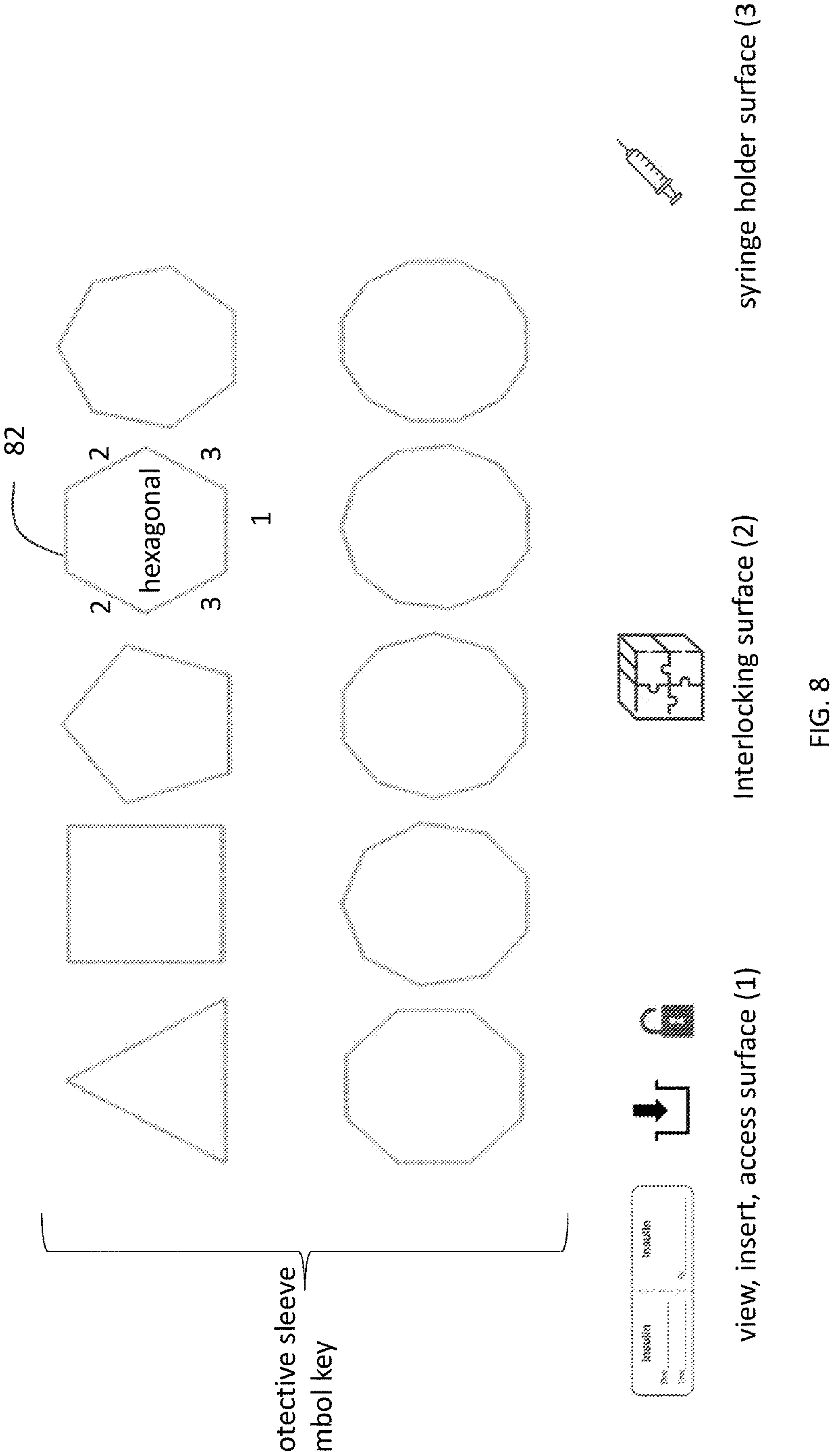
FIG. 8 depicts a symbol key for exemplary polygonal configurations and surface feature arrangements in accordance with an aspect of the invention.

A symbol key, which serves as a high-level abstraction of the configuration-utility of the protective sleeve, is provided in FIG. 8. The figure offers clarity on the various polygonal configurations of the sleeve design. Each shape, carefully curated, is not only aesthetically appealing but plays a vital role in functionality and utility. The decision to opt for a polygonal shape stem from the objective of enhancing surfaces for increased usability and to circumvent the issue of the sleeve rolling when placed on flat surfaces. As shown in FIG. 8, the hexagon is the preferred polygonal given the number of available and opposable surfaces 82. The opposable syringe-holder assembly surfaces (3) and opposable interlocking surfaces (2) are both viable, while still allowing a patient or caretaker to at least one of view a vial, insert a vial, access a vial, access the syringe—all while multiple vials are chained together. Moreover, these polygonal configurations are tailored to optimize storage efficiencies. When stacked or stowed, their form promotes a compact and ordered arrangement, minimizing wasted space. Another advantage of these shapes is the ergonomic aspect; their contours naturally fit the human hand, providing a comfortable and assured grip.

Even the seemingly simple cylindrical sleeve design carries its set of advantages. While it doesn't offer flat surfaces like its polygonal counterparts, it utilizes strategic points on its circular layout to position the front view aperture, the opposable interlocking components, and an optional syringe holder. It's imperative to highlight that the interlocking and syringe holder features don't necessarily need to be in opposable positions. Depending on the chosen interlocking mechanism, opposability might not always be a requirement.

A noteworthy advantage of these designs is their versatility. Depending on the number of surfaces or points available, as seen in a hexagonal design, the sleeves can cater to a diverse range of functionalities: from view apertures and access points to insertion gateways and interlocking mechanisms. Optionally, they can also incorporate syringe holder assemblies.

While this specification contains many specific execution details, these should not be interpreted as limitations on the scope of any inventions or of what may be claimed, but rather as descriptions of features specific to particular embodiments of particular inventions. Certain features that are described in this specification in the context of separate embodiments can also be implemented in combination in a single embodiment. Contrariwise, various features that are described in the context of a single embodiment can also be implemented and interpreted in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

The invention claimed is:

1. A protective sleeve apparatus for multiple vial carriage or vial chaining, said apparatus comprising:

a unitary pliable first sleeve having a longitudinal axis configured for protectively encasing a medical vial, wherein the first sleeve is further comprised of:

at least one surface or point on the first sleeve with an aperture extending through a wall of the sleeve for at least one of a vial insertion, vial access for drawing vial contents, and viewing a label and/or quantity of content in the vial; and a first interlocking member disposed on a lateral side of the first sleeve and a complementary second interlocking member disposed on an opposing lateral side of the first sleeve, wherein the first interlocking member is configured to removably engage the complementary second interlocking member of a second sleeve in a lateral direction transverse to the longitudinal axis to form a linear chain of independently encased vials, and wherein each sleeve remains individually removable from the chain.

2. The protective sleeve apparatus of claim 1, wherein the complementary interlocking members employ a positive and negative feature coupling mechanism.

3. The protective sleeve apparatus of claim 1, wherein a portion of the first sleeve comprising the interlocking member is made of a pliable material comprising at least one of a thermoplastic polyurethane or silicone.

4. The protective sleeve apparatus of claim 1, wherein the interlocking member and the first sleeve are comprised of the same pliable material with similar tensile values.

5. The protective sleeve apparatus of claim 2, wherein the positive feature coupling mechanism is disposed on a fixed side of the first sleeve and includes a protruding, interlocking member.

6. The protective sleeve apparatus of claim 2, wherein the negative feature coupling mechanism is disposed on a fixed opposing side of the first sleeve and includes a recessed, interlocking member.

7. The protective sleeve apparatus of claim 2, wherein the positive feature coupling mechanism is disposed on the lateral side and the negative feature coupling mechanism on the opposing lateral side, enabling interlocking with the second sleeve.

8. The protective sleeve apparatus of claim 1, further comprising a housing for a syringe.

9. The protective sleeve apparatus of claim 1, wherein the multiple vial carriage or vial chaining comprises at least two vials.

10. A protective sleeve apparatus for vial chaining, said apparatus comprising a first sleeve fabricated from at least one of an elastomeric, thermoplastic, synthetic rubber, specialty polymer, and composite material conferring the first sleeve with at least one of a shock-absorption, flexibility, thermal stability, and UV-resistant property; and a means for interlocking said first sleeve with at least a second sleeve, said means for interlocking including at least one of a positive and negative feature interlocking, magnetic coupling, clips, hook and loop closure, snap-fit connection, and bonded assembly disposed on at least one of opposable side walls for each of the first and second interlocked sleeves, whereby the interlocked sleeves enable vial chaining.

* * * * *